US008835126B2

(12) United States Patent
Filer

(10) Patent No.: US 8,835,126 B2
(45) Date of Patent: Sep. 16, 2014

(54) TRITIATED PLANAR CARBON FORMS

(75) Inventor: Crist N. Filer, Somerville, MA (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 270 days.

(21) Appl. No.: 13/161,114

(22) Filed: Jun. 15, 2011

(65) Prior Publication Data
US 2011/0306084 A1 Dec. 15, 2011

Related U.S. Application Data

(60) Provisional application No. 61/354,781, filed on Jun. 15, 2010.

(51) Int. Cl.
| | |
|---|---|
| C07C 33/18 | (2006.01) |
| C07C 9/00 | (2006.01) |
| C12Q 1/02 | (2006.01) |
| G01N 33/534 | (2006.01) |
| G01N 23/00 | (2006.01) |
| A61K 51/02 | (2006.01) |
| B82Y 30/00 | (2011.01) |
| B82Y 40/00 | (2011.01) |
| C01B 31/02 | (2006.01) |
| C01B 31/04 | (2006.01) |

(52) U.S. Cl.
CPC .............. *B82Y 40/00* (2013.01); *B82Y 30/00* (2013.01); *C01B 2202/02* (2013.01); *C01B 31/0273* (2013.01); *C07B 2200/05* (2013.01); *C01B 31/0484* (2013.01); *Y10S 977/75* (2013.01); *Y10S 977/752* (2013.01); *Y10S 977/742* (2013.01); *Y10S 977/734* (2013.01)
USPC ............. 435/29; 977/750; 977/752; 977/742; 977/734; 568/808; 585/16; 250/362; 250/395

(58) Field of Classification Search
USPC ....... 435/29; 568/808; 585/16; 250/395, 362; 977/750, 742, 734, 752
See application file for complete search history.

(56) References Cited

U.S. PATENT DOCUMENTS

| | | | |
|---|---|---|---|
| 6,203,814 B1 | 3/2001 | Fisher et al. | |
| 7,671,230 B2 * | 3/2010 | Bolskar et al. | ............ 560/82 |
| 2007/0231252 A1 | 10/2007 | Loan et al. | |
| 2009/0147906 A1 | 6/2009 | Cooper et al. | |

FOREIGN PATENT DOCUMENTS

| | | | | |
|---|---|---|---|---|
| WO | WO-2009018092 A1 | 2/2009 | | |
| WO | WO2009/092913 | * | 7/2009 | ............ A61K 51/00 |

OTHER PUBLICATIONS

Khong, A. et al. (Apr. 2000). "From.3He@C.sub.60 to 3H@C.sub.60: Hot-Atom Incorporation of Tritium in C.sub.60," Journal of Physical Chemistry A vol. 104, pp. 3940-3943.*

Liu et al., Tritiation of Semiconductor Materials for Micropower Application, Fusion Science and Technology, 54, 627-630 (2008).*
Liu Z., et al., "In Vivo Biodistribution and Highly Efficient Tumour Targeting of Carbon Nanotubes in Mice," Nature Nanotechnology, vol. 2, pp. 47-52, Jan. 2007.
Kam N., et al., "Functionalization of Carbon Nanotubes via Cleavable Disulfide Bonds for Efficient Intracellular Delivery of siRNA and Potent Gene Silencing," J. Am. Chem. Soc., vol. 127, Jun. 2005.
Liu Z., et al., "siRNA Delivery into Human T Cells and Primary Cells with Carbon-Nanotube Transporters," Angew. Chem. Int. Ed., vol. 46, 2023-2027, 2007.
Sumio Lijima et al; Helical Microtubules of Graphitic Carbon; Nature Publishing Group, vol. 354; 1991; pp. 56-58.
Andraski et al.; Plant-Based Plume-Scale Scale Mapping of Tritium Contamination in Desert Soils; Vadose Zone Journal 4; 2005; pp. 819-827.
Andraski et al.; Plume-Scale Testing of a Simplified Method for Detecting Tritium Contamination in Plants and Soils; Vadose Zone Journal, 4(3), 819-827, 2005.
Akzonobel; OMS 06.388.01; Jan. 2006; pp. 1-14.
Falorni et al.; Mild Reduction of Carboxylic Acids to Alcohols Using Cyanuric Chloride and Sodium Borohydride; Tetrahedron Letters 40; 1999; pp. 4395-4396.
Minyaev et al.; Planar and Pyramidal Tetracoordinate Carbon in Organoboron Compounds; J. Org. Chem; 2005; pp. 6693-6704.
Lam et al; Pulmonary Toxicity of Single-Wall Carbon Nanotubes in Mice 7 and 90 Days After Intratracheal Installation; Toxicological Sciences 77; 2004; pp. 126-134.
Liu et al.; Drug Delivery with Carbon Nanotubes for In Vivo Cancer Treatment; www.cancerres.aacrjournals.org; 2008; pp. 6652-6660.
Prof. Dr. Burkhard Konig; Reduction Reactions; Institut fur Organische Chemie, Uni Regenburg; pp. 1-20 Mar. 6, 2009.
Yoon; Selective Reduction of Organic Compounds with Aluminium and Boron Hydrides; Pure & Appl. Chem., vol. 68, No. 4; 1996; pp. 843-848. Lam; Pulmonary Toxicity of Single-Wall Carbon Nanotubes in Mice 7 and 90 Days After Intratracheal Installation; Toxicological Sciences 77;2004; pp. 126-134.
Zhuang Liu et al; Cancer Research vol. 68, pp. 6652-6660; 2008.
Ito, A. et al., "TH/7-1 Molecular Dynamics Simulation of Chemical Sputtering of Hydrogen Atom on Layer Structured Graphite," 22nd Fusion Energy Conference, Oct. 17, 2008.

* cited by examiner

*Primary Examiner* — Paul A Zucker
*Assistant Examiner* — Mark Luderer
(74) *Attorney, Agent, or Firm* — Gifford, Krass, Sprinkle, Anderson & Citkowski, P.C.

(57) ABSTRACT

Tritiated planar carbon forms and their production are provided. Methods are provided for the stoichiometrically controlled labeling of planar carbon forms capitalizing on normal flaws of carboxylic acids ubiquitously present in commercial preparations of these planar carbon forms. Alternative methods include generation of a metallated intermediate whereby a metal is substituted for hydrogen on the carbon backbone of a planar carbon form. The metalized intermediate is then reacted with a tritium donor to covalently label the planar carbon form. The tritiated planar carbon forms produced are useful, for example, for determination of a biological property or environmental fate of planar carbon forms.

29 Claims, 1 Drawing Sheet

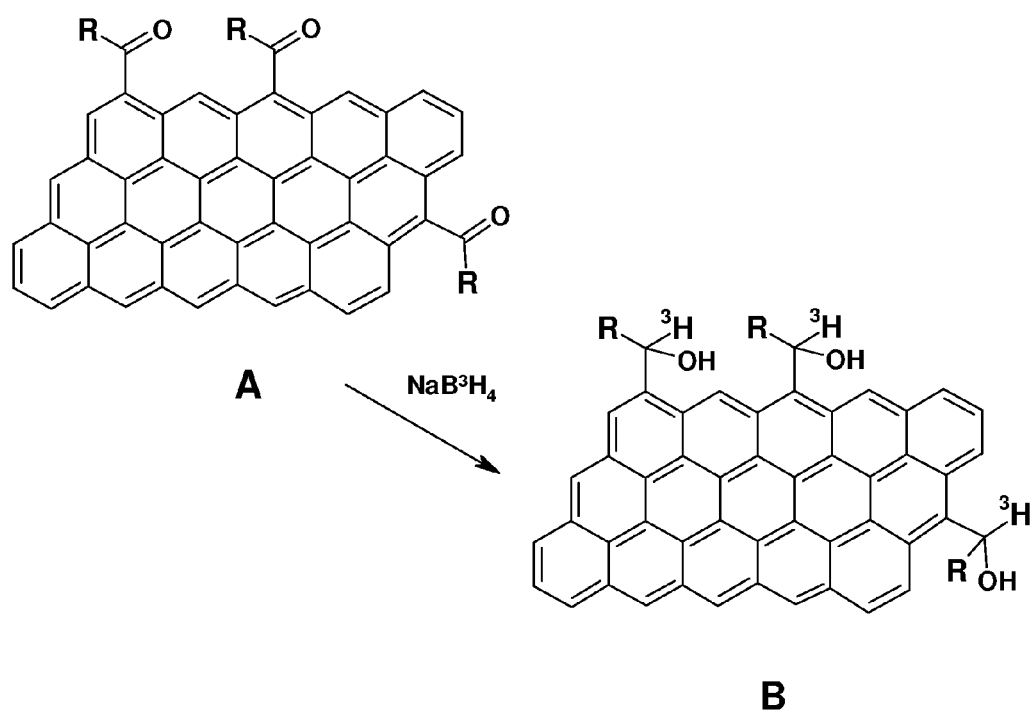

TRITIATED PLANAR CARBON FORMS

CROSS-REFERENCE TO RELATED APPLICATIONS

This application depends from and claims priority to U.S. Provisional Application No. 61/354,781 filed Jun. 15, 2010, the entire contents of which are incorporated herein by reference.

FIELD

The present disclosure relates to tritiated planar carbon forms such as carbon nanotubes and graphene, and methods for their production and use. Planar carbon forms are provided with specific and stoichiometrically controlled tritium labels.

BACKGROUND

There is increasing interest in planar carbon forms, especially single and multi-walled carbon nanotubes. Carbon nanotubes were first synthesized by Ijima in 1991 using an arc-discharge reaction. Much of the focus of current studies focus is on thinly fabricated mono molecular sheets of carbon called graphene. These and other planar carbon forms are subjects of a great deal of interest, in particular owing to their mechanical strength, conductor or semi-conductor properties, and thermal properties.

Future commercial applications for these substances could be widespread and diverse, likely ranging from the electronics industry to health sciences and medicine. The manufacture and use of planar carbon forms, however, currently presents several unknowns including environmental impacts, the ability to sequester the product in a production facility, and the pharmacokinetics, pharmacodynamics, biodistribution, and toxicology of these materials in the body. Of particular interest is the biodistribution of planar carbon forms in an organism after accidental or therapeutic administration or exposure to planar carbon forms. Several in vitro studies suggest that the inhalation of carbon nanotubes can present a significant risk to the lungs. Similarly, in vivo studies suggest that carbon nanotubes may cause extensive inflammation in the lungs potentially leading to fibrosis. Moreover, functionalization of planar carbon forms and modifications to improve biocompatibility of these materials may actually increase the toxicity associated with these materials.

Unfortunately, studies of biodistribution, pharmacodynamics, etc., are difficult to perform and typically rely on extensive modifications of the base planar carbon form such as by extensive labeling that may lead to alteration of the actual properties of the carbon forms relative to that of planar carbon forms in their unmodified state. Thus, simple and directly labeled planar carbon forms and methods of their production are needed.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A tritiated planar carbon form is provided with one or more atoms of tritium covalently associated with a planar carbon form. The tritium is optionally a member of a side chain (e.g. $C^3H_2OH$, $O^3H$), other covalently tethered side chain or ligand, or directly associated with the carbon backbone of the planar carbon form. Tritiated planar carbon forms optionally have a specific activity at or in excess of 0.5 Ci/matom. A tritiated planar carbon form optionally takes the form of any planar carbon form known in the art, illustratively nanotubes (single-walled or multi-walled) or graphene.

Also provided are methods for producing tritiated planar carbon forms. Some embodiments include reducing one or more surface carboxyl groups to surface tritiated alcohols with a reducing agent optionally including $^3H$. A reducing agent, optionally tritiated diborane or tritiated lithium aluminum hydride, are used to reduce the carboxylic acids on the planar carbon form. A suitable organic solvent, optionally anhydrous, is optionally used.

In other embodiments, a method for producing tritiated planar carbon forms includes treating a metallated planar carbon form with a tritium donor such as tritiated water. Optionally, the method includes metallating a planar carbon form by reacting a planar carbon form with a metal donor under conditions suitable for displacement of a hydrogen on a surface of the planar carbon form. A strong aryl or alkyl-metal base is optionally used. Illustrative metals include Li, Be, Mg, Al, Ti, and Tl.

Also provided are methods of using tritiated planar carbon forms in the measurement of the biological or environmental fate of planar carbon forms using a sample obtained from a subject or from the environment. A sample can be, for example, an environmental sample, manufacturing sample, biological sample, medical sample and other sample suspected of containing a planar carbon form, such as a carbon nanotube and/or graphene. Specific exemplary environmental samples include an air sample, a soil sample, a water sample, a plant sample, an animal sample and a tissue sample.

In some embodiments methods for the use of tritiated planar carbon forms in the measurement or determination of the biological fate of a planar carbon form such as determining one or more pharmacological characteristics such as absorption, distribution, metabolism, excretion or biodistribution of a planar carbon form following exposure of a subject to a planar carbon form.

BRIEF DESCRIPTION OF THE DRAWINGS

FIG. 1 represents an exemplary schematic of portions of a labeling reaction for acyl-functionalized planar carbon forms according to one embodiment.

DETAILED DESCRIPTION OF EMBODIMENTS

The following description of particular embodiment(s) is merely exemplary in nature and is in no way intended to limit the scope of the invention, its application, or uses, which may, of course, vary The invention is described with relation to the non-limiting definitions and terminology included herein. These definitions and terminology are not designed to function as a limitation on the scope or practice of the invention but are presented for illustrative and descriptive purposes only.

The labeled planar carbon forms described herein are useful, for example, in diagnostic studies, environmental studies, and biodistribution studies.

Several methods of manufacturing planar carbon forms such as carbon nanotubes are known in the art. Illustratively, Ebbesen et al., *Nature,* 1992, 358, 220-222, describe a method for making multi-walled carbon nanotubes in gram quantities.

Carbon nanotubes are currently available in several forms that vary according to the diameter, the length, and the linking of the carbon atoms. Illustratively, carbon nanotubes are available in small diameter (0.8 to 1.2 nm) single-wall nanotubes such as those sold under the trade name HiPco® by NanoIntegris (Skokie, Ill.), multi-wall structures (Multi-Wall Carbon Nanotubes: MWCNTs), or as planar graphite sheets such as graphene. In general, the diameter of carbon nanotubes is between 0.5 and 30 nm and their length reaches several micrometers or more.

General methods for the preparation of carbon-14 labeled multi-wall nanotubes have been described. (D. Georgin et al., *J Am. Chem. Soc.*, 2009; 131, 14658-14659; WO/2009/092913; U.S. Application Publication No. 2011/0038794). Tritium labeled nanotubes and graphene, however, present a previously unappreciated alternative to carbon-14, especially with regard to higher specific activity. Although tethering of a specific tritiated ligand to a carbon nanotube has been described (Z. Liu et al., *Cancer. Res.*, 2008; 68:6652-6660), these materials may suffer from different biological or environmental fates or characteristics relative to the unmodified planar carbon forms. There has been no description of a method to tritiate the surface of the planar carbon forms themselves. Direct labeling of the planar carbon forms, optionally via a small side chain optionally with a molecular weight less than 500 Da, 400 Da, 300 Da, 200 Da, or 100 Da, or with a molecular weight less than 10 Da different from a carboxyl, would not suffer from variant or unrepresentative metabolism in an organism that may arise from the presence of the other labels previously associated with these planar materials.

In manufacturing processes of planar carbon forms, such as carbon nanotubes and graphene, the product includes some level of carbon or metal based impurities. The isolation of crude planar carbon forms leaves a material with a surface that contains randomly placed carboxyl groups ($CO_2H$) as accepted structural defects. These "flawed" sites are termed "Stone-Wales defects" and are thought to be important for the beneficial plasticity of planar carbon forms. It has been reported that even after extensive base washing, these carboxyl groups persist in significant quantity (K. A. Worsley et al., *J. Am. Chem. Soc.*, 2009, 131, 18153-18158).

The inventors have recognized that these flawed sites are useful for labeling planar carbon forms without the need for extensive modification to the structure of the planar carbon form typically representative of prior labeling processes. Also, the labeled planar carbon forms may be produced if desired from commercially available material. Such a labeled planar carbon form can be used, for example, directly, or supplemented to a commercial preparation of planar carbon forms as a tracer, for studies of the fate of such carbon forms during or after manufacturing or exposure to the environment or to an organism.

As used herein, the term "planar carbon form" means a single, generally one carbon atom thick polymeric carbon material. Illustrative examples of a planar carbon form include multi-walled carbon nanotubes, single-walled carbon nanotubes, and graphene, such as those known in the art. In the event that a planar carbon form is eventually produced that lacks flawed sites, or to increase the number of carboxylic acid flaws on the planar carbon form, the base material is optionally functionalized to include additional carboxylic acid illustratively by methods described in U.S. Pat. No. 6,203,814.

In some embodiments, the reduction of carboxyl groups present in planar carbon forms with tritium affords high specific activity tritiated alcohols in place of some of the carboxyl groups, thereby providing a general planar carbon form tritiation protocol. A method targeting carboxyl groups includes reacting a planar carbon form including one or more carboxylic acid groups on its surface, with a reducing agent capable of reducing a carboxylic acid so as to produce a tritiated planar carbon form with at least one atom of tritium associated with the surface.

The inventive methods are illustrated herein with respect to nanotubes (NT) generally, and to single-walled carbon nanotubes (SWNT) when used as a specific example, for the sole purpose of exemplifying the invention. The methods taught herein are equally applicable to other types of planar carbon forms.

Illustratively, a NT is obtained from a commercial source such as from NanoLab, Waltham, Mass. The NT is optionally suspended in an organic solvent, optionally an organic solvent that is substantially free of water. Illustrative examples of such an organic solvent include tetrahydrofuran (THF), dimethoxyethane (DME), diethylether ($Et_2O$), other appropriate solvents as recognized by one of skill in the art, or combinations thereof. The choice of an appropriate solvent is readily envisioned by one of skill in the art based on the reducing agent used to tritiate the planar carbon form.

In some embodiments, a planar carbon form is reacted with a reducing agent to convert one or more carboxylic acids on the surface of the planar carbon form to a tritium containing side chain such as an alcohol containing side chain. In some embodiments the carboxylic acid is reduced to a methanol side chain ($CH_2OH$). One or more atoms of tritium are incorporated into the side chain. Illustratively, the labeled side chain is $CH_2OH$ where at least one of the hydrogens is a tritium. Illustratively, the labeled side chain is $C^3H_2OH$.

A reducing agent is any reducing agent capable of reducing a carboxylic acid when used under appropriate conditions. Such reducing agents are commonly referred to as strong reducing agents. Examples of reducing agents include those that react as nucleophiles, but a reducing agent may act as an electrophile such as diborane. Illustrative reducing agents include diborane ($B_2H_6$), lithium aluminum hydride (LAH; $LiAlH_4$), diisobutylaluminium hydride (DiBAL; $(i-Bu_2AlH)_2$), sodium borohydride (when used under the appropriate conditions), Red-Al ($Na[H_2Al(OCH_2CH_2OMe)_2]$), borohydride exchange resin (BER) or other reducing agents such as described by Yoon, *Pure & Appl. Chem.*, 1996; 68:843-848, among others, and combinations thereof. In some embodiments, the reducing agent is tritiated as a proton donor for the association of a tritium with a planar carbon form. A tritiated reducing agent is optionally formed in situ. Illustratively, diborane is an explosive gas such that its formation in solution provides additional safety. The formation of tritiated diborane is optionally achieved by reacting sodium borotritide with boron trifluoride etherate in anhydrous THF. The formed tritiated diborane is immediately available to reduce carboxylic acids on a surface of a planar carbon form.

The methods described herein provide at least one atom of tritium associated with the surface of a planar carbon form. As used herein the term "associated" means covalently attached either directly to the carbon backbone of the planar carbon form, or covalently attached to a side chain that is itself covalently attached to a planar carbon form. The term associated is exclusive of non-covalent interactions with either the backbone of the planar carbon form, or to a covalently associated backbone of a planar carbon form.

In some embodiments, a tritiated planar carbon form is created by forming an intermediate metallated planar carbon form. When a metallated intermediate of a planar carbon form is used in the preparation of a tritiated planar carbon form, the presence of carboxyl groups in the planar carbon form, e.g. in the carbon nanotube or graphene, is not essential.

Illustrative methods of metallating a carbon nanotube are illustrated in U.S. Pat. No. 6,203,814 with further methods and considerations found in March, Advanced Organic Chemistry, 3rd ed., pg. 545 et seq. A planar carbon form is reacted with a metal donor under conditions suitable for the displacement of a hydrogen on a surface of the planar carbon form and association of a metal. The metallated planar carbon form is then subsequently reacted with a tritium donor to form a tritiated planar carbon from.

Illustrative examples of metals associated with a planar carbon form to produce a metallated planar carbon form include lithium (Li), beryllium (Be), magnesium (Mg), aluminum (Al), titanium (Ti), and thallium (Tl), among others. A metallated planar carbon form is reacted with a metal donor under suitable conditions to produce a carbon metal bond (C-M). A metal donor is optionally any organometallic agent suitable of donating a metal. An exemplary organometallic agent is butyllithium.

After a planar carbon form is metallated, the metallated planar carbon from is then reacted with a tritium donor. Exemplary tritium donors include tritiated forms of water, ammonia, sodium hydroxide, ammonium hydroxide, and O-methylhydroxylamine, among others. The tritium donors are reacted with the metal planar carbon form under appropriate conditions recognized by those of skill in the art. Illustratively, thalliated planar carbon forms are reacted with a tritum donor in dioxane and triphenylphosphene. Lithiated planar carbon forms are illustratively reacted with tritiated water in THF.

In some embodiments, a planar carbon form is acyl-functionalized prior to labeling with tritium. Illustrative examples of forming acyl intermediates are described in Hirsch et al. *J. Am. Chem. Soc.,* 2011; 133:7985-7995. Suitable reactants for the formation of an acyl intermediate include carboxylic acid derivatives such as esters and acyl halides such as acyl chloride. The formation of an acyl intermediate allows for subsequent tritiation using any reducing agent suitable for the reduction of a ketone such as sodium borotritide, others described herein, among others known in the art, or combinations thereof. The resulting product is a tritiated planar carbon form with a tritium as a member of a side chain with of formula (I)

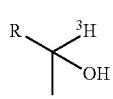

(I)

where R is any carbon containing group that results from a reduced ketone in the acyl functionalized intermediate. R is illustratively a $C_1$-$C_{30}$ alkyl, $C_1$-$C_{30}$ haloalkyl, $C_6$-$C_{30}$ aryl, $C_6$-$C_{30}$ aryl with one or more halo substituents, $C_1$-$C_{20}$ ether, and $C_6$-$C_{20}$ heterocyclic containing a heteroatom of N, O, or S, among other groups known in the art. An illustrative example of a tritiated planar carbon form according to one embodiment of the invention is found in FIG. 1.

The stoichiometry of the tritiation can be adjusted to control the number of the carboxyl groups that are converted to tritiated alcohols as well as the planar carbon specific activity and surface characteristics. The amount of tritium is controlled by adjusting the amount of tritium source (e.g. tritiated reducing agent, or tritium donor) relative to the planar carbon form, adjusting the reaction conditions such as the optimum solvent, temperature, time of reaction, etc. so as to adjust the level of tritium incorporated into a tritiated planar carbon form.

The inventive methods of producing a tritated planar carbon form result in the formation of a tritiated planar carbon form with the desired amount of incorporated tritium. The sites of surface tritiated alcohols, or other tritiated side chains, can themselves function as alternative locations for anchoring additional planar carbon form chemical modifications such as association with drugs, peptides, nucleic acids, labels (e.g. fluorescent, biotin, etc.), or other desired molecules. Planar carbon forms can also be prepared with alternative surface functionality. Exemplary methods for preparing tritiated planar carbon forms optionally provide specific activities adjustable by the user, including specific activities exceeding 0.5 Ci/matom, optionally exceeding 1.0 Ci/matom. In some embodiments, the specific activity is 0.1 to 2 Ci/matom or any value or range therebetween. Optionally, the specific activity is 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, or more Ci/matom. An advantage of the methods is that the resulting specific activity of the tritiated planar carbon form can be tailored to as a user desires. As such lower or higher specific activities are similarly within the scope of the invention.

The tritiated planar carbon forms have at least one atom of tritium covalently associated with a surface of a planar carbon form. In some embodiments, a tritium atom is associated with a planar carbon form through or by a functional or non-functional side chain. Illustrative examples of a functional side chain include those capable of serving as reactant in subsequent reactions such as an alcohol, amine, acid, or other functional group. In some embodiments, a tritium is a member of a $CH_2OH$, OH, $NH_2$, SH, or other group with at least one hydrogen replaced with tritium. Illustratively, a tritium is present as $C^3H_2OH$ or $O^3H$.

A tritiated planar carbon form is in any form of a source planar carbon form. Illustratively, the invention provides a tritiated graphene, tritiated SWNT, tritiated MWNT, or other. A tritiated planar carbon form optionally has one or more additional functional sites for the incorporation of additional molecules such as drugs, proteins, nucleic acids, labels, or others known in the art. Such additional molecules are either covalently or otherwise associated with a tritiated planar carbon form. Illustrative examples of additional molecules include the like of those described in Liu, et al., *Cancer Res.,* 2008; 68(16):6652-60 among others known in the art. Any additional molecule associatable with a planar carbon form including a tritium is operable to be associated with a planar carbon form.

Tritiated planar carbon forms are optionally used in methods of detecting a planar carbon form in a sample. Such methods can be used to monitor any property of a planar carbon form, illustratively, aerosolization, absorbption, biodistribution, pharmakodynamics, transfer, chemical or physical breakdown, or other property of a planar carbon form. A method of detecting a planar carbon form includes supplementing a planar carbon form source with a tritiated planar carbon form. "Supplementing" as used herein is defined as adding a tritiated planar carbon form to a planar carbon form source that is itself tritiated, is otherwise labeled or modified, or is free of label or other modification, or by excluding any adding when the planar carbon form source is itself tritiated. As such, the word supplementing does not require addition of tritiated planar carbon form to a source of tritiated planar carbon form when the source is itself tritiated. Supplementing a tritiated planar carbon form to a planar carbon form source produces a labeled source.

The labeled source is then detected by detecting the presence of a tritiated planar carbon form in a test sample derived from the labeled source. As used herein, the term "derived" is meant to be related to the labeled source by origin. A test sample is derived from a labeled source if it contains or may contain a portion of a planar carbon form present in the labeled source. Illustratively, a test sample is derived from a labeled source if it is or is a portion of an organism that was exposed to the labeled source. Detecting is optionally by measuring the amount or activity of a tritiated planar carbon form, or identifying the presence of a tritiated planar carbon form in the test sample by detecting the emission of a beta particle from a tritiated planar carbon form in excess of control background measured simultaneously with or sequentially with the test sample.

A test sample is optionally obtained from a subject or from the environment. A subject as used herein is optionally: a human or non-human primate; bovine; equine; murine; a cell; a tissue; plant such as a tree, crop plant, weed, or portion thereof; insect; or other biological source. A test sample from a subject is illustratively blood, plasma, serum, sputum, saliva, lung aspirate, bile, urine, feces, vaginal secretions, semen, cerebral spinal fluid, skin, vitreous, hair, or other portion of an organism.

A test sample is optionally an environmental sample. Illustrative examples of an environmental sample include water, mud, soil, air, manufacturing sample, other environmental sample, or combinations thereof.

The presence or absence of a planar carbon form in a test sample is determined by detecting the presence or absence of a tritiated planar carbon form in the test sample. Detecting is by any method operable to detect the presence of tritium in a sample. Illustrative procedures of detecting tritium include liquid scintillation counting or autoradiography. These methods are known in the art. Illustrative methods are described by Hunt and Foote, *Radiation Res.*, 1967; 31:63-73; Shu et al., *Nuclear Instruments and Methods in Physics Research Section A: Accelerators, Spectrometers, Detectors and Associated Equipment*, 2004; 521:423-29; Andranski, et al., *Journal of Environmental Quality*, 2003: 32:988-995; and Andranski et al., *Vadose Zone Journal*, 2005; 4:819-827. In some embodiments, flow through gas detector systems, liquid scintillation counters, mass spectrometers, or other instruments are used.

In some embodiments, detecting a tritiated planar carbon form is used to determine one or more pharmacological characteristics of a planar carbon from source that is or is substantially similar to (e.g. similar side chains, additional groups, etc.) the tritiated planar carbon form source. A pharmacological characteristic is optionally a property of a planar carbon form. As an example, the biodistribution of a planar carbon form is determined in an organism. A subject is exposed to a labeled source for an exposure time. Exposure is optionally by administration by any known method such as intravenous, oral, inhalation, subcutaneous, absorption, or by exposure to air or other gas including a labeled source. Following a distribution time, a test sample is obtained from the subject by any suitable method. The test sample is subjected to a detection process to detect the presence or absence of a tritiated planar carbon form in the test sample. Optionally, a test sample is obtained from blood, urine, saliva or other sources from a single subject. Each sample is tested for the presence or absence of a planar carbon form. The presence or absence of a tritiated planar carbon form in a test sample is indicative of the biodistribution of the planar carbon form source.

Other properties of a planar carbon form in a subject or environmental sample include absorption, distribution, metabolism, or excretion. These properties are not limiting, and any property of a planar carbon form interacting with a subject or the environment are determinable by the methods.

Various aspects of the present invention are illustrated by the following non-limiting examples. The examples are for illustrative purposes and are not a limitation on any practice of the present invention. It will be understood that variations and modifications can be made without departing from the spirit and scope of the invention. Reagents illustrated herein are readily obtained in the commercial marketplace.

EXAMPLE 1

Carbon Nanotube Tritium Labeling With $B_2{}^3H_6$

Single wall carbon nanotubes (10 mg, NanoLab product D1.5L1-5-COOH) are suspended in 2 mL of dry THF along with 7 mg (0.18 mmol) of high specific activity sodium borotritide at −80° C. A solution of 30 μL (0.24 mmol) of boron trifluoride etherate in 0.3 mL of dry THF is then added via syringe with stirring. The solution is gradually warmed to ambient temperature and stirred an additional 4 hours. After this time the reaction is cooled to 0° C. and sufficient 1 N HCl is added to quench excess $B_2{}^3H_6$. Volatile tritium is removed by evaporation of several 3 mL portions of ethanol. The solid tritiated single wall carbon nanotube product is then stirred with three 3 mL portions of distilled water, centrifuged, and the supernatant water is carefully removed by syringe. The specific activity of the tritiated carbon nanotubes is measured gravimetrically by weighing a known amount of the product and dissolving it in a convenient solvent with radioactivity measurement by liquid scintillation counting (PerkinElmer Tri-Carb 3100 TR).

The reactions are repeated using multi-walled nanotubes and graphene as source planar carbon forms with similar results.

EXAMPLE 2

Carbon Nanotube Tritium Labeling With $LiAl^3H_4$

A single-walled carbon nanotube source (10 mg, NanoLab product D1.5L1-5-COOH) is suspended in 2 mL of dry THF. The nanotube solution is added to a solution of $LiAl^3H_4$ (2.5 equivalents) in anhydrous THF at 0° C. and stirred at room temperature for 1 h. The reaction is quenched by the addition of 1M HCl (dropwise) at 0° C., and the solvent is removed in vacuo. The product is dissolved in EtOAc and extracted with saturated aqueous $NaHCO_3$, 1M HCl, $H_2O$, brine, and dried over $MgSO_4$. The reactions are repeated using anhydrous $Et_2O$ or DME as the solvent. Other reactions are performed similar to those described by Tanaka et al., *J. Med. Chem.*, 1995: 38(15):2860-2866. Excellent yields of tritiated planar carbon forms are obtained and the specific activity determined gravimetrically by weighing a known amount of the product and dissolving it in a convenient solvent with radioactivity measurement by liquid scintillation counting (PerkinElmer Tri-Carb 3100 TR).

The reactions are repeated using multi-walled nanotubes and graphene as source planar carbon forms with similar results.

EXAMPLE 3

Carbon Nanotube Tritium Labeling Using DiBAL

A single-walled carbon nanotube source (10 mg, NanoLab product D1.5L1-5-COOH) is dissolved in anhydrous $Et_2O$ (3 mL/mmol) and cooled to 0° C. A solution of i-Bu$_2$Al$^3$H (2.5 equivalents) in hexane (1M) is added dropwise, and the reaction mixture is maintained at 0° C. for 1 hour. The labeling is quenched by addition of saturated aqueous NaHCO$_3$ followed by stirring for 18 h at room temperature and subsequent dilution with EtOAc. The organic layer is washed with brine, dried over MgSO$_4$, filtered and concentrated to give the tritiated carbon form. The reaction is repeated using anhydrous THF, DCM, or CHCl$_3$ as alternative compatible solvents. Good yields of tritiated planar carbon forms are obtained and the specific activity determined gravimetrically by weighing a known amount of the product and dissolving it in a convenient solvent with radioactivity measurement by liquid scintillation counting (PerkinElmer Tri-Carb 3100 TR).

The reactions are repeated using multi-walled nanotubes and graphene as source planar carbon forms with similar results.

EXAMPLE 4

Carbon Nanotube Tritium Labeling Using Borane Dimethylsulfide

A single-walled carbon nanotube source (10 mg, NanoLab product D1.5L1-5-COOH) (1 equivalent) dissolved in anhydrous THF (3 mL/mmol) is subjected to dropwise addition of tritiated borane-dimethyl sulfide complex (2 equivalent) in THF (1 mL/mmol), cooled to 0° C., and stirred for 1 hour substantially as described by Dhanoa, et al., *J. Med. Chem.*, 1993: 36:4239-4249. The labeling is quenched by addition of 1N HCl followed by stirring for 18 h at room temperature and subsequent dilution with EtOAc. The organic layers are combined and washed with saturated aqueous NaHCO$_3$, brine, and dried over MgSO$_4$, filtered and concentrated to give the tritiated carbon form. Good yields of tritiated planar carbon forms are obtained and the specific activity determined gravimetrically by weighing a known amount of the product and dissolving it in a convenient solvent with radioactivity measurement by liquid scintillation counting (PerkinElmer Tri-Carb 3100 TR).

The reactions are repeated using multi-walled nanotubes and graphene as source planar carbon forms with similar results.

EXAMPLE 5

Carbon Nanotube Tritium Labeling With Tritiated Water

Single wall carbon nanotubes (1 gram, NanoLab product D1.5LI-5-COOH) are lithiated by processes similar to those described in U.S. Pat. No. 6,203,814 under an argon atmosphere. 10 mg of the lithiated single wall carbon nanotubes are suspended in 2 mL of dry THF and cooled to –80° C. High specific activity tritiated water (37.4 mg, 1.7 mmol, 100 Ci) is then added to the reaction with stirring. The solution is then gradually warmed to ambient temperature and stirred an additional 4 hours. After this time, the reaction is cooled to 0° C. and sufficient 1 N HCl is added. Volatile tritium is removed by evaporation of several 3 mL portions of ethanol. The solid tritiated single wall carbon nanotube product is then stirred with three 3 mL portions of distilled water, centrifuged, and the supernatant water is carefully removed by syringe. The specific activity of the tritiated carbon nanotubes is measured gravimetrically by weighing a known amount of the product and dissolving it in a convenient solvent with radioactivity measurement by liquid scintillation counting (PerkinElmer Tri-Carb 3100 TR).

The reactions are repeated using multi-walled nanotubes and graphene as source planar carbon forms with similar results.

EXAMPLE 6

Acyl Functionalization and Labeling of Carbon Nanotube With Sodium Borotritide Single wall carbon nanotubes (5 mg, NanoLab product D1.5L1-5-COOH) are acyl functionalized by a modified Birch reaction essentially as described by Hirsch et al. *J. Am. Chem. Soc.*, 2011; 133:7985-7995. Briefly, the carbon nanotubes are dispersed in anhydrous THF by ultrasonication for 30 min. Reductive conditions are created by condensing ammonia following cooling to –78° C., addition of lithium metal at 5 equivalents relative to mole carbon in the nanotubes, and evaporation of the ammonia. The nanotubes are then reacted with a carbonyl electrophile at two equivalents to form the acyl-functionalized carbon nanotubes. Three carbonyl electrophiles are individually used: 1) methyltrifluoroacetate; 2) methylbenzoate; and 3) 3,4-dichlorobezoyl chloride; although other carboxylic acid derivatives will also yield acyl-functionalized intermediates.

The acyl-functionalized nanotubes are suspended in 2 ml dry THF with 7 mg (0.18 mmol) of high specific activity sodium borotritide at –80° C. The solution is gradually warmed to ambient temperature and stirred an additional 4 h. After this time the reaction is cooled to 0° C. and sufficient 1 N HCl is added to quench excess sodium borotritide. Volatile tritium is removed by evaporation of several 3 mL portions of ethanol. The solid tritiated single wall carbon nanotube product is then stirred with three 3 mL portions of distilled water, centrifuged, and the supernatant water is carefully removed by syringe. The specific activity of the tritiated carbon nanotubes is measured gravimetrically by weighing a known amount of the product and dissolving it in a convenient solvent with radioactivity measurement by liquid scintillation counting (PerkinElmer Tri-Carb 3100 TR).

The reactions are repeated using multi-walled nanotubes and graphene as source planar carbon forms with similar results.

EXAMPLE 7

Biodistribution of Carbon Nanotubes in a Subject

B6C3F1 mice (male, 2 months old) are obtained from Charles River Laboratories (Indianapolis, Ind.) and housed in a vivarium with a 12-hour light-dark cycle. The animals are provided food and water ad libitum. The animals are maintained under these conditions for at least one week prior to exposure to carbon nanotubes.

Single wall carbon nanotubes (1 gram, NanoLab product D1.5LI-5-COOH) are supplemented with tritiated carbon nanotubes prepared as described in any of Examples 1-5. In one study, carbon nanotubes are administered carbon nanotubes by mock inhalation, thereby requiring preparation of samples similar to those expected to be found during a manufacturing process e.g. fine dust suspensions. The fine dust suspensions are prepared in mouse serum essentially as described by Lam et al., *Toxicological Sci.*, 2004; 77:126-134 and references described therein.

A labeled sample of carbon nanotubes is administered to the mice by intratracheal instillation essentially as described by Lam et al., *Toxicological Sci.*, 2004; 77:126-134 and references described therein. Briefly, restrained and anesthetized animals are subjected to a 1 cm incision on the ventral neck. A 0, 0.1 or 0.5 mg dose of nanotubes in serum are injected into the trachea via a small hole close to the larynx. The incision is sutured and the mice allowed to rest for at least one hour prior to obtaining test samples.

Alternatively, a supplemented solution of carbon nanotubes in saline (0.1 mg/ml) is injected into the tail vein of the mice (200 microliters).

Test samples (lung tissue, blood, urine, brain tissue, liver tissue) are obtained from sacrificed mice by appropriate procedures at 1 hour, 12 hours, 7 days, and 90 days following exposure (and also each hour for 1 to 5 hours for blood exposure) and solubilized in lysis buffer (1% SDS, 1% Triton X-100, 40 mM Tris acetate, 10 mM EDTA, 10 mM DTT). A portion of each test sample is added to liquid scintillation solution and the level of tritium is measured essentially as described by Mahin and Lofberg, *Anal. Biochem.*, 1966; 16:500-509. The presence of tritiated nanotubes in each test sample indicates the biodistribution or excretion of the nanotubes at each time point tested. The biodistribution of the nanotubes in each biological compartment is calculated.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A planar carbon form comprising one or more atoms of tritium covalently associated with said planar carbon form, wherein said tritium is present as a component of —CH$_2$OH group, wherein at least one of said hydrogens is replaced with tritium, or said tritium is present as

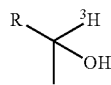

wherein R is any carbon group that results from a reduced ketone in the acyl functionalized intermediate.

2. The planar carbon form of claim 1 wherein said tritiated planar carbon fowl has a tritium specific activity in excess of 0.5 Curies per milliatom.

3. The planar carbon form of claim 1 wherein the planar carbon form is selected from the group carbon nanotube and graphene.

4. The planar carbon form of claim 1 wherein the planar carbon form is a nanotube.

5. The planar carbon form of claim 4 wherein the nanotube is single-walled.

6. The planar carbon form of claim 4 wherein the nanotube is multi-walled.

7. A method for producing the tritiated planar carbon form of claim 1 comprising:
reacting a planar carbon form comprising one or more carboxylic acid groups on a surface of said planar carbon form, with a reducing agent capable of reducing a carboxylic acid so as to produce a tritiated planar carbon form with at least one atom of tritium associated with said surface.

8. The method of claim 7 wherein said reducing agent includes at least one $^3$H.

9. The method of claim 7 wherein the reducing agent is selected from the group B$_2$$^3$H$_6$ and LiAl$^3$H$_4$.

10. The method of claim 7 wherein said planar carbon form is the group comprising a carbon nanotube and graphene.

11. The method of claim 7 wherein said reducing agent is B$_2$$^3$H$_6$ wherein said B$_2$$^3$H$_6$ is formed in situ.

12. The method of claim 7 wherein said reacting is in an organic solvent.

13. The method of claim 12 wherein said organic solvent is tetrahydrofuran.

14. A method for producing the tritiated planar carbon form of claim 1 comprising:
forming a metallated planar carbon form by reacting a planar carbon form with a metal donor under conditions suitable for displacement of a hydrogen on a surface of said planar carbon form; and
reacting said metallated planar carbon form with tritiated water to form a tritiated planar carbon form.

15. The method of claim 14 wherein said forming comprises contacting the planar carbon form with a strong aryl or alkylmetal base along with said metal donor.

16. The method of claim 14 wherein said planar carbon form is metallated with a metal selected from the group lithium, beryllium, magnesium, aluminum, and titanium.

17. The method of claim 14 wherein the planar carbon form is selected from the group carbon nanotube and graphene.

18. The method of claim 14 wherein the metal is Li.

19. A method for producing the tritiated planar carbon form of claim 1 comprising:
reacting an acyl functionalized planar carbon form having a surface with a reducing agent capable of reducing a ketone so as to produce a tritiated planar carbon form with at least one atom of tritium associated with said surface.

20. The method of claim 19 wherein said reducing agent includes at least one $^3$H.

21. The method of claim 19 wherein the reducing agent is selected from the group B$_2$$^3$H$_6$, LiAl$^3$H$_4$, and NaB$^3$H$_4$.

22. The method of claim 19 wherein said planar carbon form is selected from the group carbon nanotube and graphene.

23. The method of claim 19 wherein said reacting is in an organic solvent.

24. The method of claim 23 wherein said organic solvent is tetrahydrofuran.

25. A method of detecting the planar carbon form in a sample comprising:
supplementing a planar carbon form source with the tritiated planar carbon form of claim 1 to produce a labeled source; and
detecting the presence or absence of a planar carbon form in a test sample derived from said labeled source by measuring the presence or absence of a beta particle emission from said sample.

26. The method of claim 25 wherein said sample is selected from the group an environmental sample, an air sample, a soil sample, a manufacturing sample, a medical sample, a biological sample, a plant sample, a tissue sample, and an animal sample.

27. The method of claim 25, further comprising determining one or more pharmacological characteristics of a biological system from said detecting.

28. The method of claim 27, wherein said pharmacological characteristic is selected from the group absorption, distribution, metabolism, excretion, and biodistribution.

29. The method of claim 25 wherein the detecting is by subjecting at least a portion of said sample to a method selected from the group liquid scintillation counting and autoradiography.

* * * * *

UNITED STATES PATENT AND TRADEMARK OFFICE
CERTIFICATE OF CORRECTION

PATENT NO.         : 8,835,126 B2
APPLICATION NO.    : 13/161114
DATED              : September 16, 2014
INVENTOR(S)        : Filer Page 1 of 1

It is certified that error appears in the above-identified patent and that said Letters Patent is hereby corrected as shown below:

In the Claim:

Column 11, claim 2, line 59, Delete "fowl", Insert --form--

Signed and Sealed this
Sixteenth Day of June, 2015

Michelle K. Lee
*Director of the United States Patent and Trademark Office*